United States Patent [19]
Frye et al.

[11] 3,954,823
[45] May 4, 1976

[54] INTERCONVERSION OF STEREOISOMERIC CYCLOORGANOSILOXANES

[75] Inventors: Cecil L. Frye; David E. Spielvogel, both of Midland, Mich.

[73] Assignee: Dow Corning Corporation, Midland, Mich.

[22] Filed: June 2, 1975

[21] Appl. No.: 583,304

[52] U.S. Cl. .................. 260/448.2 E; 260/448.8 R
[51] Int. Cl.² ...................... C07F 7/02; C07F 7/08; C07F 7/20
[58] Field of Search ........................... 260/448.2 E

[56] References Cited
UNITED STATES PATENTS 3,332,974  7/1967  Bostick....................... 260/448.2 E
3,493,595  2/1970  Strasser et al................ 260/448.2 E

*Primary Examiner*—Paul F. Shaver
*Attorney, Agent, or Firm*—Robert F. Fleming, Jr.

[57] ABSTRACT

Stereoisomers of cycloorganosiloxanes are interconverted without siloxane bond redistribution by reacting the cyclic siloxane with anhydrous zinc chloride, zinc bromide, ferric chloride, aluminum chloride or aryl phosphonium chlorides in the presence of nitro compounds or aryl phosphate esters as solvents. A typical example is the conversion of 2,6-trans-diphenylhexamethylcyclotetrasiloxane to the 2,6-cis-isomer by heating in 2-nitropropane solvent in the presence of anhydrous zinc chloride.

17 Claims, No Drawings

INTERCONVERSION OF STEREOISOMERIC CYCLOORGANOSILOXANES

BACKGROUND OF THE INVENTION

It is known that Lewis acids such as ferric chloride-hexahydrate and aluminum chloride are catalysts for the polymerization of lower molecular weight siloxanes to gums for use in making siloxane elastomers. This reaction was first set forth in U.S. Pat. No. 2,448,756. The reaction involves the condensation of silanol groups and the rearrangement of silicon-oxygen-silicon bonds. It is also known that zinc chloride catalyzes the reaction of acyl anhydrides or carboxylic acids with siloxanes to produce acyl-ended organopolysiloxanes. This reaction involves the splitting of a siloxane bond. However, as far as applicants can determine no one has taught the interconversion of stereoisomers as hereinafter defined.

It is the object of this invention to provide a commercially feasible method of converting one stereoisomer of cyclic organosiloxanes into another stereoisomer without disturbing the order of siloxane units in the molecule or increasing the molecular weight of the siloxane.

STATEMENT OF THE INVENTION

This invention relates to a method for converting stereoisomeric cyclosiloxanes from one stereoisomer to another which comprises contacting a siloxane which is capable of forming cis and trans isomers with anhydrous $MX_n$ where X is chlorine or bromine, M is zinc, iron, or aluminum and $n$ is the valence of the metal, or aryl phosphonium halides in the presence of a solvent of the group organic nitro compounds and aryl phosphate esters under conditions where such interconversion will take place without appreciable distribution of the siloxane structure.

The interconversion of this invention is an equilibrium phenomenon and the proportion of cis and trans isomers at equilibrium varies with the different cyclics. As with any chemical equilibrium, the reaction can be forced in the desired direction by removing the desired isomer from the reaction zone. This can be done continuously by removing the desired isomer as it is formed. For example, the reaction can be carried out at a temperature above the boiling point of the desired isomer. Alternatively, the entire reaction mixture can be cooled or removed from the reaction zone, the desired isomer separated and the undesired isomer returned to the reaction zone for further interconversion. The separation of the isomers can be done either by distillation, crystallization or solvent extraction or any other convenient method. Any of these procedures can be done either continuously or batchwise.

The type of siloxanes which can be employed in this invention include any cyclic siloxane having two different substituents, bonded to the silicon through silicon-carbon bonds, on at least two silicon atoms in the molecule. These include homopolymeric cyclics such as phenylmethylcyclotetrasiloxane or trifluoropropylmethylcyclotetrasiloxane or mixed isomers having different siloxane units such as 2,6-diphenylhexamethylcyclotetrasiloxane or 2,4-diphenylhexamethylcyclotetrasiloxane*. The cyclic siloxanes can be of any size such as trimers, tetramers, hexamers, octamers or higher with the trimers, tetramers and pentamers being the ones of greatest commercial importance.

*In the numbering system used in this application, the oxygen atom is the number one atom.

The substituents on the silicon atom can be any substituent attached to the silicon through a silicon-carbon bond which does not inactivate the catalyst. These substituents include monovalent hydrocarbon radicals such as alkyl radicals, such as methyl, ethyl, propyl or octadecyl; alkenyl radicals such as vinyl, allyl and hexenyl; cycloaliphatic hydrocarbon radicals such as cyclopentyl, cyclohexyl, cyclohexenyl or methylcyclohexyl aryl hydrocarbon radicals such as phenyl, tolyl, or naphthyl and aralkyl hydrocarbon radicals such as benzyl, beta-phenylethyl, or 2-phenylpropyl. The substituents also include any halogenated hydrocarbon radical such as chloromethyl, chloroethyl, 3,3,3-trifluoropropyl, chlorophenyl, bromophenyl, bromotolyl, fluorophenyl and beta-(chlorophenyl)ethyl.

Specific examples of operative cyclosiloxanes are 2,6-(chlorophenyl)hexamethyl cyclotetrasiloxane, 2,4-(3-chloropropyl)tetramethyl cyclotrisiloxane, tetracyclohexyltetramethyl cyclotetrasiloxane, 2,4-dimethyltetraphenyl cyclotrisiloxane, tetraethyltetraxenyl cyclotetrasiloxane, trivinyltrimethyl cyclotrisiloxane, 2,4-dioctylhexamethyl cyclotetrasiloxane and pentamethylpentaphenyl cyclopentasiloxane.

The cyclic materials employed as starting materials in this invention are well known and numerous examples of them are shown, for example, in U.S. Pat. Nos. 3,830,712 and 3,652,628, both of which are incorporated herein by reference.

It has been found that the interconversion proceeds in certain solvents. These are any organic nitro compound such as aliphatic nitro compounds such as nitromethane, nitropropane, nitrobutane, nitrooctane, cycloaliphatic nitro compounds such as nitrocyclohexane, nitrocyclopentane, and nitromethylcyclohexane and aromatic nitro compounds such as nitrobenzene, nitrotoluene, p-chloronitrobenzene or dimethyl bis(nitrophenoxy) silane. Other operative solvents are aryl phosphate esters such as triphenyl phosphate, tricresyl phosphate, tri(isopropylphenyl)phosphate, trisnitrophenyl phosphate, butyldiphenyl phosphate and trischlorophenyl phosphate.

The catalysts employed herein are anhydrous zinc chloride or zinc bromide, anhydrous iron chloride, anhydrous aluminum chloride and aryl phosphonium halides such as triphenylphosphonium chloride, benzyl triphenylphosphonium bromide, naphthyltriphenylphosphonium chloride, beta-phenylethyltritolylphosphonium chloride and xenyltriphenylphosphonium bromide.

The concentration of catalyst or of solvent is not critical nor is the temperature or pressure. Thus, temperatures can vary from room temperature to 250°C. or above. The catalyst concentration is preferably from 1 to 50 mole percent based on the moles of siloxane present and the solvent concentration is preferably above 10 percent based on the weight of the siloxane. The optimum conditions vary with the choice of catalyst, solvent and cyclic. This means that with a particular cyclic, a particular catalyst and a particular solvent, the reaction may go at room temperature whereas with the same cyclic and solvent and a different catalyst the reaction may require 150°C. or above. For this reason, no meaningful numerical limitations on temperature, catalyst concentration or solvent concentration can be given.

The cyclics prepared by the method of this invention are of known utility which can vary from intermediates in the preparation of organopolysiloxane elastomers to the use of the cyclics as biologically active compounds.

The following examples are illustrative only and should not be construed as limiting the invention which is properly delineated in the appended claims.

EXAMPLE 1

To a spinning band distillation flask was added 9.03 g. of diphenylhexamethylcyclotetrasiloxane consisting of 96.1 percent by weight of the 2,6-trans isomer*, 0.27 g. of anhydrous zinc chloride and 9.52 g. of tricresyl phosphate. The solution was heated for 4 hours at 220°C. The sample was distilled at 160° to 162°C. at 4-7 mm. while successive cuts were taken and analyzed by SCOT (i.e. Support Coated Open Tubular) GLC analysis using the technique described in *Acta Pharmicologica Et Toxicologica*, Vol. 36, Supplement III, page 27, March 1975. The results are shown in the table below:

| Distillation Cuts | Weight Grams | GLC Area % 2,6-Trans | % 2,6-Cis |
|---|---|---|---|
| 1 | 1.8 | 49.15 | 50.85 |
| 2 | 1.35 | 52.48 | 47.52 |
| 3 | 3.12 | 59.53 | 40.47 |
| 4 | 0.86 | 70.22 | 29.78 |

*The remainder of the material was 2,6-cis, 2,4-cis and 2,4-trans isomers, all three of which are usually present in trace amounts in the starting cyclotetrasiloxane.

There was no build-up of rearrangement products.

EXAMPLE 2

In each case shown below recrystallized 2,6-trans isomer of diphenylhexamethylcyclotetrasiloxane was heated with the anhydrous catalyst shown under the conditions shown and in each case the trans isomer was converted to the 2,6-cis isomer. In each case the solvent was used in amount of 50 percent by weight solvent and 50 percent by weight siloxane.

| Catalyst | Catalyst/Siloxane Ratio | Solvent | Temperature | Time | Results by GLC Area % 2,6-Cis | 2,6-Trans |
|---|---|---|---|---|---|---|
| Benzyltriphenyl phosphonium chloride | 1/8.4 | Triphenyl phosphate | 170±20°C. | 18 hrs. | 45.4 | 50.9 |
| Aluminum chloride | 1/13.5 | Triphenyl phosphate | 60±5°C. | 4.5 hrs. | 4.0 | 95.6 |
| Ferric chloride | 1/17.5 | Triphenyl phosphate | 60±5°C. | 4.5 hrs. | 48.5 | 50.3 |
| Ferric chloride | 1/45.2 | 2-Nitro propane | 25°C. | 2 hrs. | 47.9 | 50.4 |
| Aluminum chloride | 1/33 | 2-Nitro propane | 55°C. | 2 hrs. | 10±5% | 90±5% |
| Zinc chloride | 1/10 | Tris-Nitro-* phenyl phosphate | 155±5°C. | 4 hrs. | 24.4 | 71.5 |

*Solvent used 45 percent by weight and 55 percent by weight siloxane.

In each case after completion of the run, the reaction mixture was cooled, washed with water to remove the catalyst and solvent and then dissolved in n-hexane. The n-hexane layer was put through the GLC.

The difference between the total percent of 2,6-cis and trans and 100 percent represents the amount of redistribution products and/or impurities in the starting siloxane. It can be seen that no appreciable redistribution of siloxane bonds took place in any of these runs.

EXAMPLE 3

In each case 4.2 g. of nitromethane and 4.2 g. of trans-2,6-diphenylhexamethylcyclotetrasiloxane were mixed with the amounts of zinc chloride shown below and in each case the mixture was heated in a closed container at 90°C. for the times shown.

| Run No. | % Zinc Chloride Based on Weight of Siloxane | 64 hrs. cis | trans | 82 hrs. cis | trans |
|---|---|---|---|---|---|
| 1 | 10 | 54% | 46% | 52% | 48% |
| 2 | 1 | 12% | 88% | 15% | 85% |
| 3 | 5 | 51% | 49% | — | — |

In each case, the proportion of isomers in the reaction product was determined by GLC. This data shows that the equilibrium between the cis and trans isomers is essentially complete after 64 hours with 10 percent zinc chloride and with 5 percent zinc chloride. It also shows that the reaction goes with 1 percent zinc chloride but at a less rapid rate.

EXAMPLE 4

To a closed vessel was added 1 g. of 2,6-cisdiphenylhexamethylcyclotetrasiloxane, 1 g. of nitromethane and 0.05 g. of anhydrous zinc chloride. The mixture was heated in a closed container at 90°C. for 18 hours. GLC analysis indicated that the product was composed of 59 percent cis and 41 percent trans. After 42 hours the ratio was 53 percent cis and 47 percent trans. This example shows that the interconversion goes in either direction; that is, from trans to cis or from cis to trans.

EXAMPLE 5

In a closed container was mixed 1 g. of transtriphenyltrimethylcyclotrisiloxane, 1 g. of nitromethane and 5 percent zinc chloride based on the weight of the siloxane. The mixture was allowed to stand at room temperature and after 18 hours GLC analysis indicated that the cis to trans ratio was 13:87 percent and after 42 hours, the cis to trans ratio had increased to 23:77 percent which is essentially the equilibrium value. This shows that the interconversion goes even at room temperature.

EXAMPLE 6

4.2 g. of 2,6-trans-diphenylhexamethylcyclotetrasiloxane, 4.2 g. of nitrobenzene and 0.21 g. of anhydrous zinc chloride were mixed and heated at 90°C.

The extent of the interconversion as a function of time is shown in the table below by GLC analysis.

| Time | % 2,6-Cis | % 2,6-Trans |
|---|---|---|
| 2 hrs. | 3.3 | 96.7 |
| 20 hrs. | 31.4 | 68.6 |
| 24 hrs. | 34.4 | 65.6 |
| 2.8 days | 46.8 | 53.2 |
| 3.8 days | 49.0 | 51.0 |

When 75 percent nitrobenzene based on the weight of the siloxane was used, 47.8 percent cis was obtained in 20 hours.

EXAMPLE 7

2.1 g. of 2,6-trans-diphenylhexamethylcyclotetrasiloxane, 2.24 g. of 2-nitropropane and 0.18 g. of anhydrous zinc bromide were heated in a closed container at 70°C. After 15.5 hours GLC showed that the amount of 2,6-cis had increased to 45 percent.

EXAMPLE 8

A mixture of 0.49 g. of trans-tris(3,3,3-trifluoropropyl)trimethylcyclotrisiloxane, 1.42 g. of 2-nitropropane and 0.0282 g. of anhydrous $ZnCl_2$ was stirred in a closed container for 18 hours at 25°C. Water in amount equal to the volume of the reaction mixture was added to dissolve the $ZnCl_2$ and the nitropropane layer was devolatilized at 25°C. and 1 to 2 mm. pressure. $F^{19}$ NMR analysis of the residue show a cis/trans ratio of 0.09/0.91. The starting cyclic had no detectable cis isomer by $F^{19}$ NMR.

EXAMPLE 9

5.44 g. of cyclotetrasiloxane of the formula (99 percent pure)

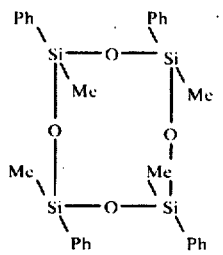

5.44 g. of nitromethane and 0.272 g. of anhydrous $ZnCl_2$ were mixed and heated at 90°C. for 64 hours. GLC analysis showed the product to be 15 percent of

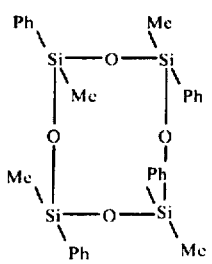

11 percent of the cis isomer and 74 percent of a mixture of the starting isomer and the isomer

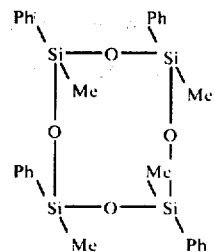

Ph is the phenyl radical and Me the methyl radical. This shows that one of the trans isomers of tetraphenyltetramethylcyclotetrasiloxane can be converted into the cis isomer and the other two trans isomers.

That which is claimed is:

1. A method of converting stereoisomeric cyclosiloxanes from one stereoisomer to another which comprises contacting a cyclosiloxane which is capable of forming cis and trans isomers with an anhydrous catalyst of the group $MX_n$ where X is chlorine or bromine, M is zinc, iron or aluminum and n is the valence of the metal or an aryl phosphonium halide in a solvent of the group organic nitro compounds and aryl phosphate esters under conditions where such conversion will take place without appreciable distribution of the siloxane structure.

2. The method of claim 1 which is carried out by feeding the undesired isomer to a heating zone, selectively removing the desired isomer from the heating zone whereby the undesired isomer is substantially completely converted to the desired isomer.

3. The method of claim 1 in which the reaction mixture is separated into the desired and undesired isomers and the undesired isomer is returned to the heating zone for further conversion.

4. The method of claim 1 in which the desired isomer is separated from the reaction mixture.

5. The method of claim 1 in which the cyclic siloxane being converted is 2,6-trans-diphenylhexamethylcyclotetrasiloxane.

6. The method of claim 2 in which the cyclic siloxane being converted is 2,6-trans-diphenylhexamethylcyclotetrasiloxane.

7. The method of claim 3 in which the cyclic siloxane being converted is 2,6-trans-diphenylhexamethylcyclotetrasiloxane.

8. The method of claim 4 in which the cyclic siloxane being converted is 2,6-trans-diphenylhexamethylcyclotetrasiloxane.

9. The method of claim 1 in which the substituents on the silicon of the siloxane are phenyl and methyl radicals.

10. The method of claim 1 in which the substituents on the silicon of the siloxane are 3,3,3-trifluoropropyl and methyl radicals.

11. The method of claim 1 in which the solvent is triphenylphosphate.

12. The method of claim 1 in which the catalyst is $MX_n$.

13. The method of claim 1 in which the catalyst is an arylphosphonium halide.

14. The method of claim 1 in which the solvent is a nitro compound.

15. The method of claim 1 in which the solvent is an aryl phosphate ester.

16. The method of claim 12 in which the catalyst is ZnCl$_2$.

17. The method of claim 12 in which the catalyst is FeCl$_3$.

* * * * *